United States Patent [19]

Miller

[11] Patent Number: 4,700,373
[45] Date of Patent: Oct. 13, 1987

[54] PLATFORMS FOR X-RAY EXAMINATION OF KNEE JOINTS

[76] Inventor: Edward H. Miller, 9795 Fox Hollow, Cincinnati, Ohio 45243

[21] Appl. No.: 858,592

[22] Filed: May 1, 1986

[51] Int. Cl.$^4$ .......................................... G03B 42/02
[52] U.S. Cl. .................................. 378/177; 378/180; 378/181
[58] Field of Search ............................ 378/177–182, 378/204, 205, 207–209; 269/322–328; 128/75, 84 R, 84 C

[56] References Cited

U.S. PATENT DOCUMENTS

| | | | |
|---|---|---|---|
| 328,460 | 10/1885 | Clark | 269/325 |
| 1,452,915 | 4/1923 | Kennedy | 128/84 R |
| 2,456,277 | 12/1948 | Heitz-Boyer | 378/179 |
| 2,926,256 | 2/1960 | Rankin | 378/181 |
| 3,631,242 | 12/1971 | Williams | 378/209 |
| 3,979,595 | 9/1976 | Merchant | 378/180 |
| 4,000,736 | 1/1977 | Bruscemi | 269/328 |
| 4,069,813 | 1/1978 | Gilula | 378/208 |

Primary Examiner—Carolyn E. Fields
Assistant Examiner—John C. Freeman
Attorney, Agent, or Firm—Kinney & Schenk

[57] ABSTRACT

Platforms are described for positioning a patient's knee for X-ray evaluation. The basic platform comprises upper and lower leg supports which are angled relative to each other at a fixed angle of 40 deg. The patient lies in a supine position with his leg flexed by the platform. Means are provided for positioning an X-ray film cassette generally parallel with a plane intersecting the bisecting the apex of the supports. An alternate platform provides means for tilting the platform, as well as a removable insert in the lower leg support, to facilitate X-ray examination of children and other person of short stature. The second platform also provides means for restraining the patient's lower leg to enable X-ray examination of the knee joint with the patient's quadrecepts muscles tensioned. A third platform is provided with a hinge connection between the upper and lower leg supports to enable X-ray evaluation of a knee at variable angles of flexion.

20 Claims, 12 Drawing Figures

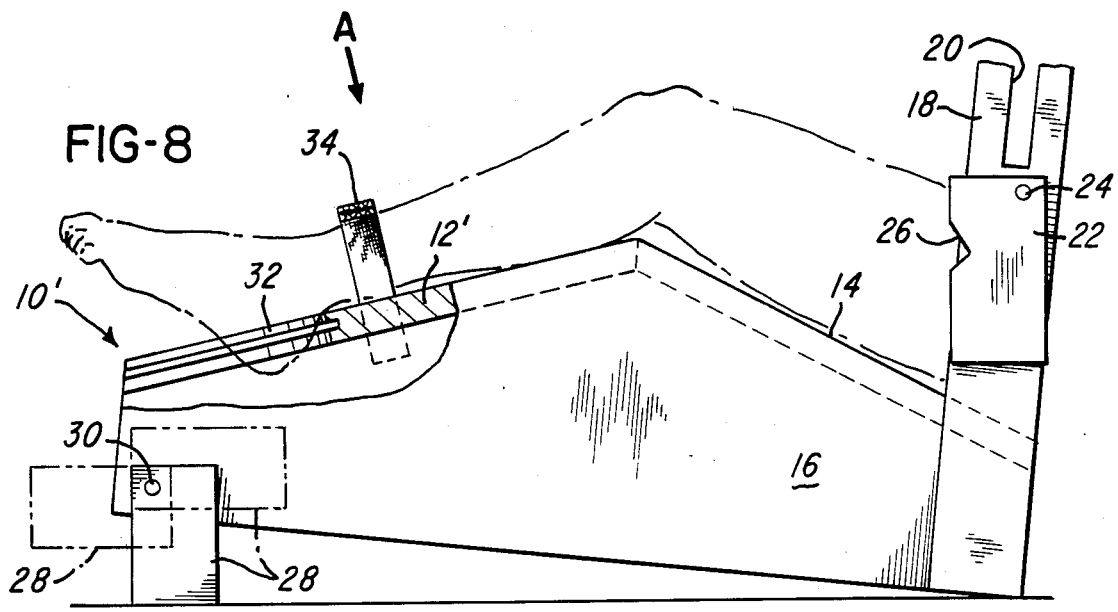
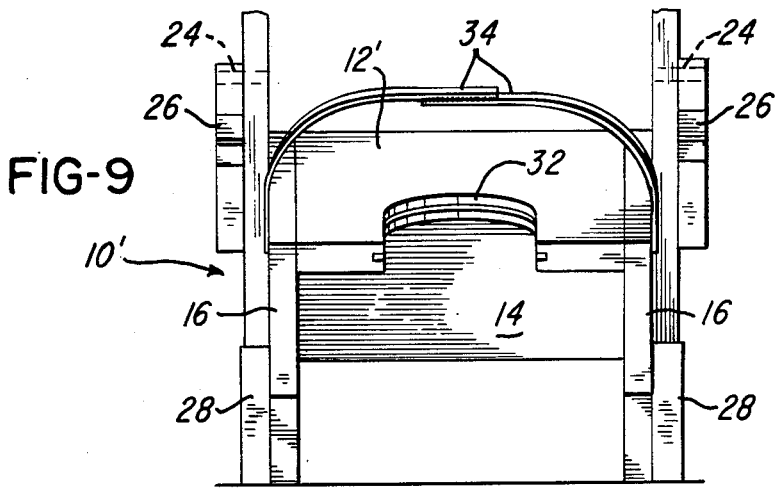

PLATFORMS FOR X-RAY EXAMINATION OF KNEE JOINTS

The present invention relates to improvements in platforms employed in positioning the knee of a patient for X-ray examination of the knee in a flexed position.

The present invention is motivated by the needs which exist in X-ray examination of the knee joint for purposes of evaluating the problems experienced by the patient and particularly those problems which focus on the tracking of the patella (knee cap) relative to the femoral suicus (a groove in the lower end of the femur, or thigh bone).

While many different X-ray views of this joint have been proposed, it is now recognized that the Merchant view is of primary importance in evaluating and deciding upon a treatment program for a malaligned knee joint. The Merchant view is taken axially, with the knee flexed, preferably to a 40 deg. angle, and with the patella generally parallel with the X-ray beam.

Early efforts to obtain X-rays of the knee in a flexed condition were truly unsatisfactory. A patient would sit on an examinatin table, with his knee flexed, and hole the film cassette by hand while the X-ray was being taken. Any accuracy in obtaining a desired angle of flexion was purely accidental. Likewise, it was virtually impossible to obtain serial X-rays which would repeat the prior relationship of the patella and femur for purposes of evaluating the effectiveness of treatment.

To some extent these problems were addressed by a knee support (more properly a lower leg support) described in U.S. Pat. No. 3,979,595. There, it is proposed that a patient lie on his back on an examination table, with his knee joints aligned at the end of the table. A support for the lower legs is placed at the end of the table. The lower legs rest on the support which is angled to provide the desired degree of flexion. An X-ray film cassette holder is provided on the lower leg support and is angled upwardly to the X-ray tube which is in an elevated position.

These proposals do represent an improvement over the prior efforts to obtain X-rays of a flexed knee joint, as is discussed in great depth in that patent. However, shortcomings still exist, not only in obtaining the Merchant view, but other views of a flexed knee. Of particular concern are such problems as greater accuracy in repetive views, patient comfort and simplicity.

Accordingly, the general object of the present invention is to improve the X-ray evaluation of a patient's knee joint problems.

Another object of the present invention is to improve the accuracy of knee X-rays and the ability to obtain repetitive X-rays illustrating a given degree of flexion.

Another object of the present invention is to obtain the above ends and additionally to obtain an evaluation of the knee when the patient's quadracepts muscles are flexed, as well as when these muscles are relaxed.

Another object of the invention is to obtain X-rays of knee joints at varying degrees of flexure and with a minimum of discomfort to the patient.

A further object of the present invention is provide a positioning platform which may be employed for patients of widely varying stature and build.

These ends are broadly obtained by a positioning platform comprising an upper leg support and a lower leg support, angled relative to each other from an apex in combination with means for positioning an X-ray film cassette generally parallel to a plane bisecting the apex of the supports.

For use with a patient who is supine on an examination table, the upper and lower leg supports and the cassette positioning means are mounted on a base which positions their apex in spaced relation above the examination table. The patient's leg is then placed on the platform with the upper leg being flexed from the hip and the knee joint aligned with the apex of the supports, so that the supports define the degree of flexion. An X-ray may then be taken by directing the beam generally horizontally throught the knee joint.

Preferably, the cassette positioning means comprise a pair of vertically slotted posts. The cassette is slid into these slots and rests on the bottoms of the slots in its lowest position. Blocks pivotally mounted on the posts may be rotated to bring support surfaces of varying heights into supporting relationship with the cassette and thus position it at incremental heights from the leg support. This feature accommodates patients of differing muscular development so that the cassette can be closely spaced from the upper, or lower, leg of the patient so that the knee joint will be projected on the film, but the cassette will be isolated from distortion due to leg movement.

One embodiment of the invention is intended for use in positioning the knees of patients of average stature. The leg supports extend from their apex to a point spaced above the bottom of the base. Preferably the lengths of the supports range from about $12\frac{1}{2}$ and $13\frac{1}{2}$ inches and the apex is spaced above the bottom of the base approximately $8\frac{1}{2}$ inches.

It is also preferred that the platform be employed to position only one leg at a time. Thus the platform is relatively narrow having a preferred width of approximately 10 inches.

To accommodate patients, particularly children, of shorter stature, means are provided for tilting the lower leg support end of the platform relative to the examination table. This shortens the distance from the apex of the supports to the table, thus permitting a shorter femur to be positioned on the upper leg support with the knee joint aligned with the apex. Additionally a removable block is provide at the free end of the lower leg support. With the block removed, the heel of a shorter patient may fall beneath the support surface, to drop the foot from a position which would interfere with an X-ray of the knee joint.

Restraining straps are provided at the lower leg support. These straps are secured over the lower leg of the patient to prevent upward movement. With the lower leg thus restrained, the patient may tension his quadracepts muscles, while the flexion defined by the angle between the supports is maintained. An X-ray may then be taken which can be compared with the condition of the joint when the muscles are relaxed, in the same degree of flexion, thus providing further, repetitive X-rays for evaluating the patient's knee problem.

The preferred angle between the upper and lower leg supports is 40 deg. for the Merchants view. However, there are other degrees of flexion which can be of value in assessing the condition of a knee joint. To this end means are provided for varying the angle between the upper and lower leg supports. This feature is also useful in minimizing patient discomfort. Thus the patient's leg may be placed on the leg supports when they are at a minimum angle. The supports are then angled in a controlled fashion to bring his knee progressively to as much as 110 deg. of flexion.

The above and other related objects and features of the invention will be apparent from a reading of the following description of preferred embodiments, with reference to the accompany drawings, and the novelty thereof pointed out in the appended claims.

In the drawings:

FIG. 8 is an elevation, with portions broken away and in section, of another positioning platform which embodies the present invention and provides adjustments to accommodate patients of different statures;

FIG. 9 is an end view the positioning platform seen in FIG. 8;

Figure 1:
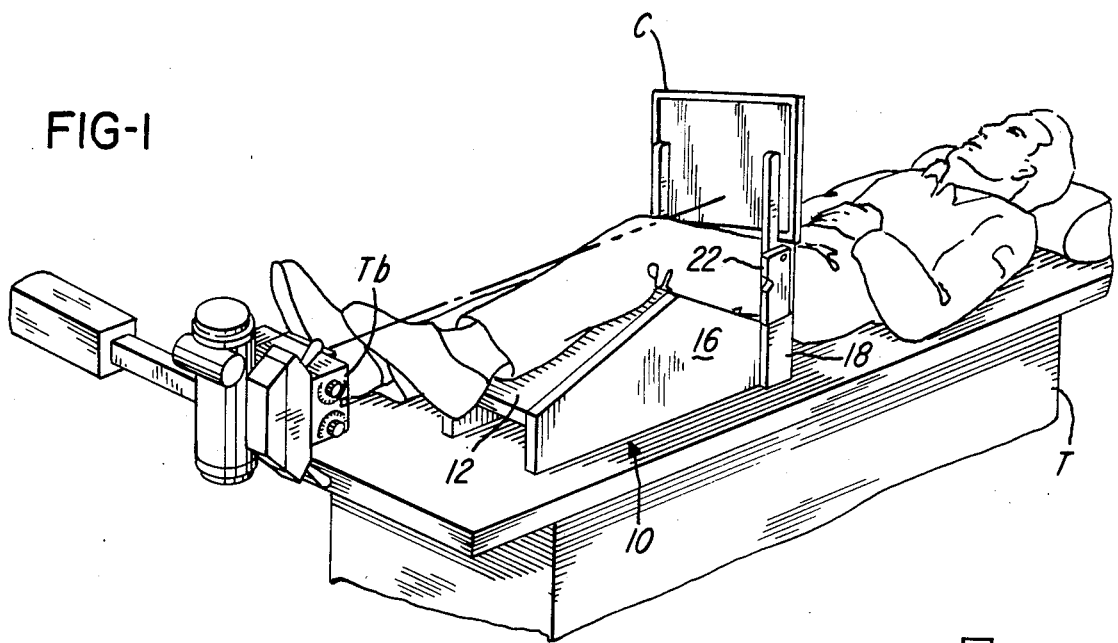
FIG. 1 is a perspective view of an positioning platform, embodying the present invention, with the knee of a patient positioned thereby, as the patient is supine on an X-ray examination table.

The present positioning platform, indicated generally by reference character 10, in its basic form, is shown in FIGS. 1-7. It is extremely simple, comprising a two angled leg supports 12 and 14, which are secured to side members 16. Posts 18 are secured to the outer surfaces of the side members 16 at one of the platform 10. The posts 18 are provided with slots 20 for receiving an X-ray cassette.

The term upper and lower leg supports, as herein used, reference the surfaces provided by boards, or plates secured to the side members 16, which also provide the outer bounds of the supporting surfaces, thus likewise functioning as supports. The side members also function as a base, spacing the supports 12 and 14 above an examination table.

The positioning platform 10 is specifically intended to provide a Merchant view of a patient's patella with 40 deg. of knee flexion. As indicated above, this view is of particular interest to orthopeadic surgeons and other practitioners in assessing malalignment syndromes, by providing a highly effective picture of the manner in which the patella tracks in the upper end of the troacular groove of the femur.

Figure 2:
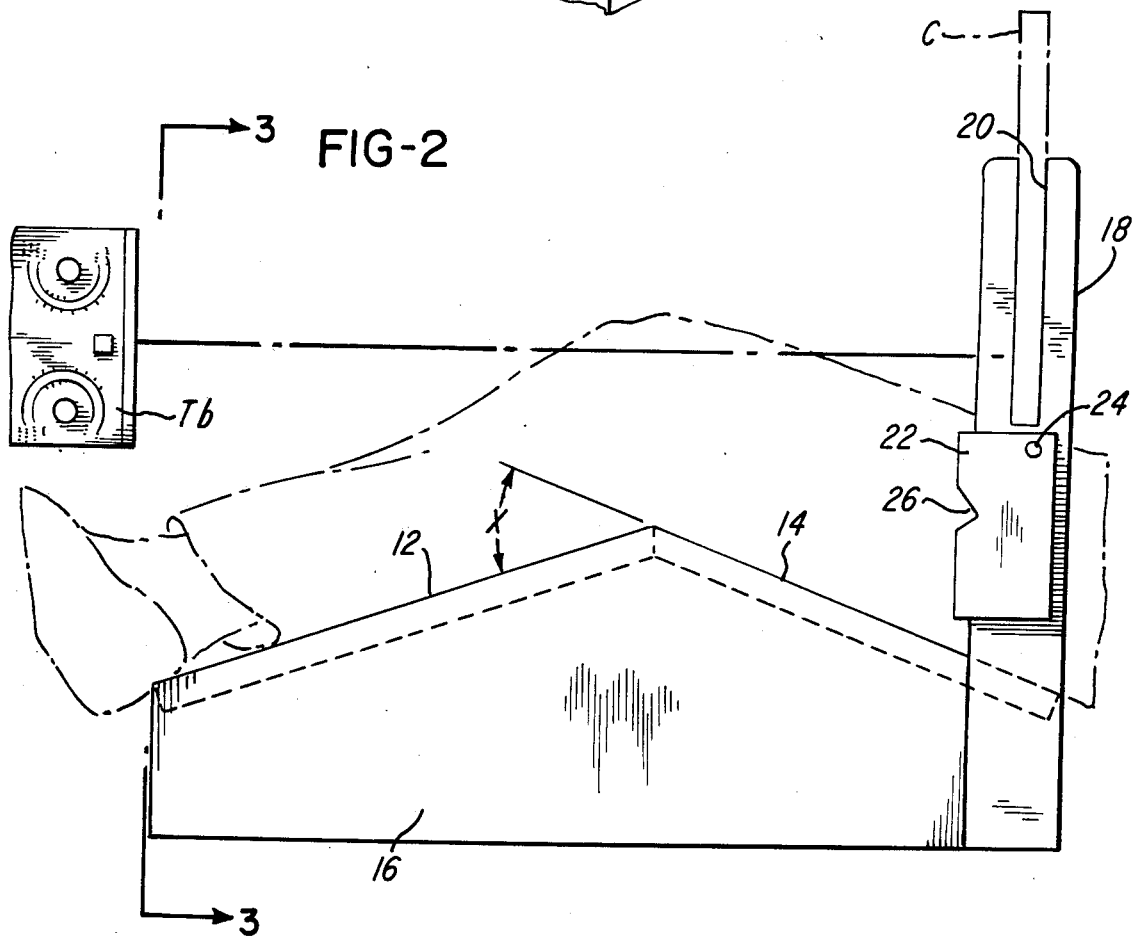
FIG. 2 is an elevation of the positioning platform.
Figure 3:
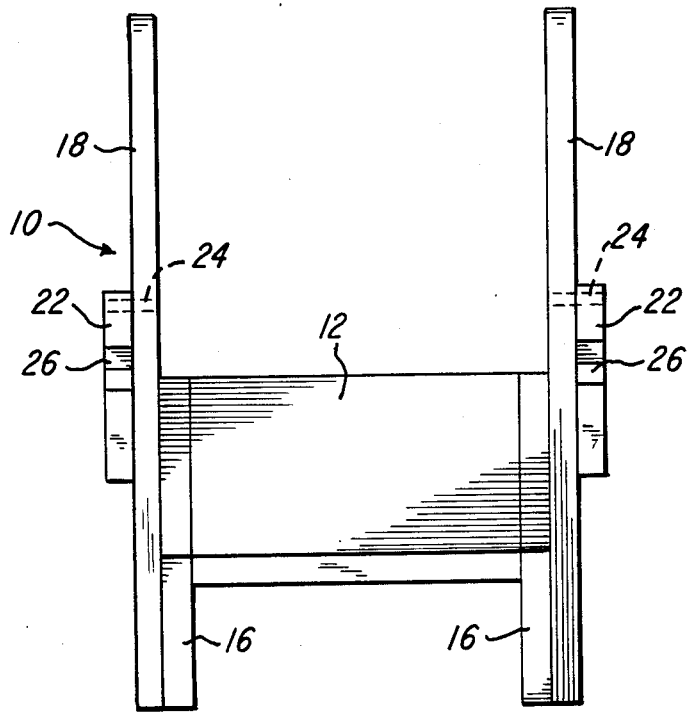
FIG. 3 is an end view of the positioning platform looking in the direction of line 3—3 in FIG. 2.
Figure 4:
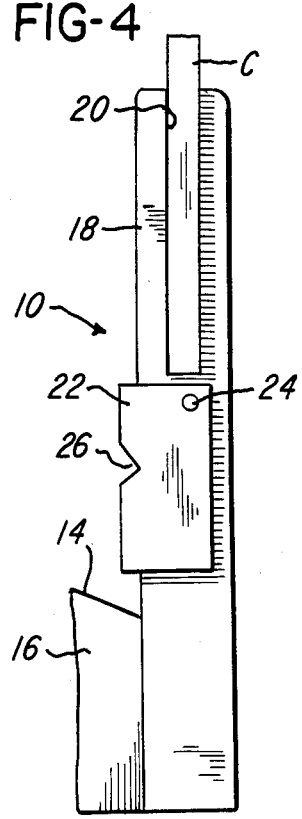
FIGS. 4, 5, 6 and 7 are elevations of a portion of the positioning platform, illustrating means for adjusting the height of X-ray film cassettes.

Use of the positioning platform 10 is illustrated in FIGS. 1 and 2. The patient lays on a standard X-ray examination table T in a supine position, i.e., on his back. The platform 10 is positioned so that the angled surface 14 supports the upper leg, or thigh, and the angled surface 12 supports the lower leg. The platform is spaced from the buttocks of the patient so that the apex formed by the surfaces 12, 14 is aligned with the axis about which the knees pivots, or flexes, with the femur and fibula generally parallel, respectively, to the surfaces 14, 12. The angle X between these surfaces is 40 deg., thus providing the desired flexion angle of the knee. In referencing the angle between upper and lower leg supports herein, it is intended that this angle is measured as in FIG. 2.

The X-ray tube Tb is positioned at the patient's feet. Its beam is aimed at the patient's patella, as indicated in FIG. 2. An X-ray cassette C is positioned in the slots 20 of posts 18, distally of the knee. The illustrated and described position and disposition of the platform and X-ray tube. Tb, enable a cephalad view of the femoral-petella joint, that is, a view looking towards the patient's head.

It will be noted that the slotted posts 18 position the X-ray film cassette parallel to a plane bisecting the apex of the supports 12, 14.

The same platform may also be used to obtain a caudad view, looking toward the foot, by reversing the platform so that the surface 12 supports the upper leg and the surface 14 supports the lower leg. The X-ray tube is then moved, or the position of the patient reversed on the table. The X-ray beam may then be directed over the body of the patient to expose the film in the cassette C which is thus disposed distally of the flexed knee.

A further feature of the platform 10 is the provision of means for adjusting the height to the X-ray film cassette C. The muscular developement of a football player, for example, is much greater than that of the ordinary person, resulting in the girths of his thighs being much greater average. In order that a clear image to be assured, it is necessary that cassette C the positively supported in the slots 20 in spaced relation from the patients thigh. It is also necessary that the cassette be as low as possible, since, with a 40 deg. flexion, the patella is not raised a great distance.

Four height positions are provided. In the lowest position, FIG. 4, the cassette simply rests in the bottoms of the slots 20. The remaining positions are provided by a pair of blocks 22 pivotally mounted, respectively, on the posts 18 by pins 24. The blocks 22 are rectangular in outline, with their lengths being about twice their widths. A notch 26 is provided in the edge of one of the long sides of each of the blocks 22. The pins 24 are disposed in one corner of each of the blocks 22.

Figure 5:
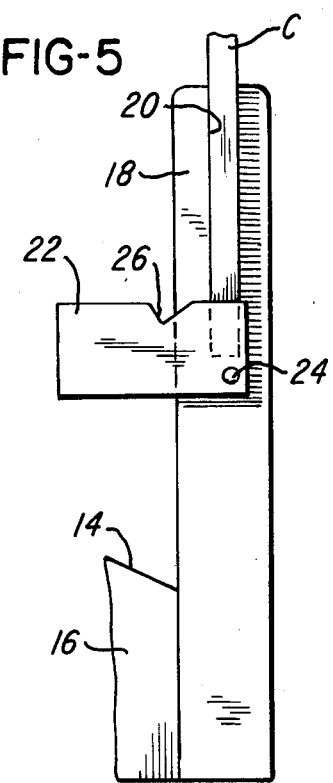

The next highest position is obtained by rotating the blocks 22 so that the shorter, width dimensions are vertically disposed, above the bottom of the slots 20. The pins are also disposed in general alignment with the slots 20. Thus the cassette C may be stably positioned on the blocks 22 as shown in FIG. 5.

Figure 6:
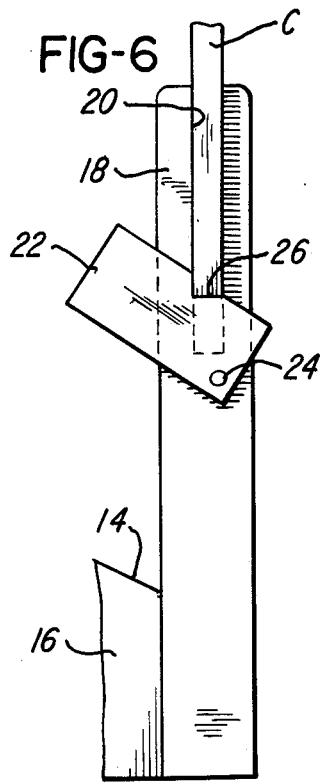
Figure 7:
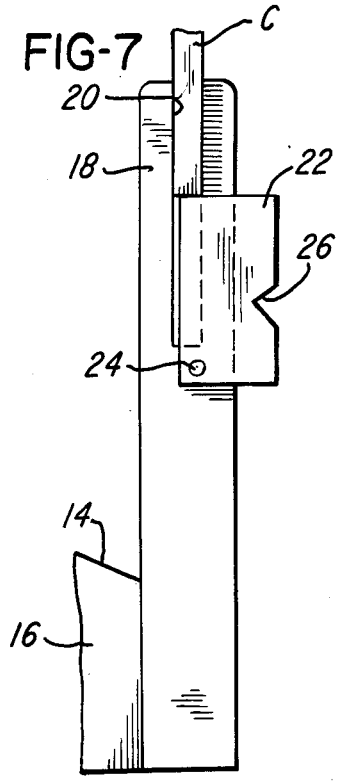

The next higher, intermediate position for the cassette is provided by rotating the blocks 22 so that the notch supporting surfaces 26 are horizontally disposed, in general alignment with and above the pins 24. The cassette C may be positioned on these surfaces and held, by its weight in this intermediate position, as illustrated in FIG. 6.

The highest position is obtained by rotating the blocks 22 so that their lengths are vertically disposed. Again the weight of the cassette resting on the blocks is sufficient to maintain it in this elevated position.

Thus, after a patient has been positioned on the examination table T, with his knee flexed over the surfaces 12 and 14. The cassette C will be inserted into the slots 20 and the blocks 22 adjusted so that it is in the lowest position, but still spaced from the patient's leg. Thus the possibility of movement of the cassette is minimized, if not eliminated, all to the end of obtaining a sharp X-ray picture.

The described platform is highly effective in providing standardized, repetitive X-rays of the femoral-patella joint and particularly the Merchant view of this joint which is highly informative in evaluating malalignment and other problems.

Not only are the X-rays repetitive for a given patient, enabling a base of comparison in evaluating the effectiveness of treatment, the standard established by this platform enables the condition of one patient's joint to be compared with the joints of other patients who have similar problems, and also with persons of similar stature, for example, whose knee joints are properly formed and function in a normal manner.

It is preferred that the platform 10 have a relatively narrow width, designed to position only one leg at a time for knee X-rays. This enables the patient to turn slightly to the side of the unflexed knee, thus causing the flexed knee, on the platform to be more naturally disposed in a desired, vertical position, without the need of a restraint. Also the single leg width of the platform facilitates turning of the foot so that it will not be aligned with the knee and block a clear view of that joint on the X-ray film.

The platform, and particularly the plates which form the support surfaces 12 and 14 are preferably formed of hard wood, such as white oak, or other radiolucent material.

The basic platform 10 is intended to serve the needs of X-raying the knee joints of the major portion of the population. That is, it is suitable for most adults, excepting those of very large and very small stature and build, and also younger children. It has been found for these purposes of a universal platform, that the apex of the supporting surfaces should be approximately $8\frac{1}{2}$ inches above the bottom of the base formed by the side members 16, which rests on the examining table. Where the angle X is 40 deg. and the angle of each of the supports 12, 14 is approximately 20 deg. relative to the bottom surfaces of the side members 16. The lengths of the supports 12 and 14 range between $11\frac{1}{2}$ and $13\frac{1}{2}$ inches. Further, it is preferred that the height of the outer ends of the supports 12 and 14 be approximately 4 inches above the bottom of the base. The width of the positioning platform is approximately 10 inches.

To accommodate taller patients, whose femur length would require a greater height of the apex of the supports 12, 14, in order for the femur to be parallel with and supported by the support 14, a block can be placed under the platform to thus raise the surfaces to the necessary height.

In a similar vein, the length of the femur of a child, or small person is too short to bring the knee joint to the apex of the supports 12, 14. To some extent, this shortcoming can be overcome by placing a mat under such a patient, to elevate his body and thus bring the knee joint to the apex of these surfaces.

Figure 10:
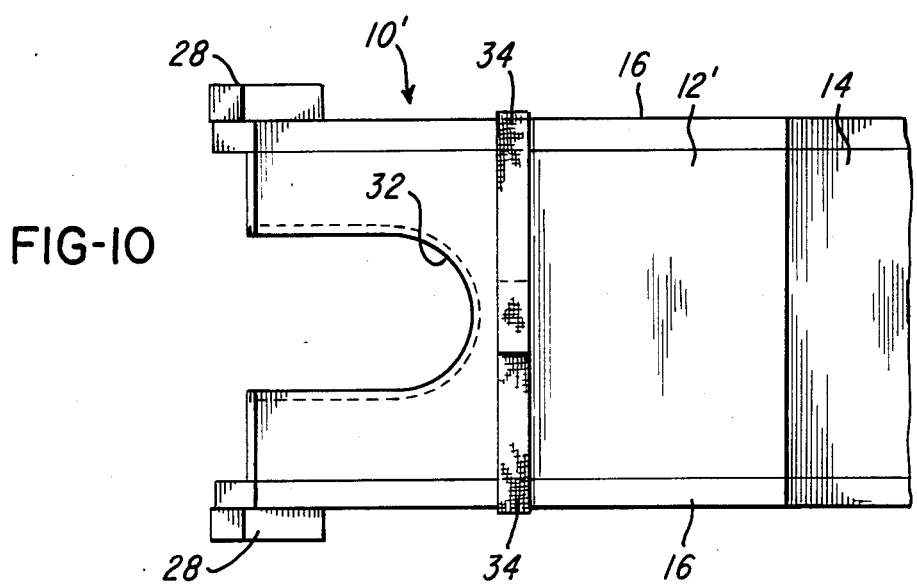
FIG. 10 is a view looking in the direction of arrow A in FIG. 8.

Another and more effective solution to accommodating patients outside the range of average statures, and particularly adapted for children, is found in the embodiment of FIGS. 8–10.

There an alternate positioning platform 10' is shown. With the exception of the support 12', its basic structural components are the same as those of platform 10 and a repeated description is not necessary.

The platform 10' is provided with a pair of blocks 28, pivotally mounted, respectively, on the side members 16, by pins 30. As with the blocks 22, the blocks 28 are rectangular in outline, with the pins 30 disposed in one corner thereof. In this embodiment, the support 12 is specifically intended to position the lower leg and the support 14 the upper leg. The blocks enable the lower leg end of the platform to be raised, to a maximum height position illustrated in FIGS. 8 and 9. This is accomplished by rotating the blocks to dispose their lengths vertically. An intermediate position can be obtained by rotating the blocks so that their shorter, widths are disposed vertically and beneath the pins 30. Finally the blocks can be rotated so that their widths, or lengths are disposed above the pins 30, so that the platform will rest on the examining table and me be used to position the knee of a patient of normal, or average stature, as previously described.

The raised position of FIG. 8 changes the angle of the support 14, to shorten the distance from the apex, of the two supports, from the examination table. Thus the femur of a child lying supine, with his hip flexed from the table, will extend to this apex and his lower leg will be positioned, with the proper flexion, by the support 12'. The intermediate position, where the widths of the blocks are vertically disposed and support the platform, would be appropriate for youths and shorter adults.

The platform further accommodates the patient of shorter stature by the provision of a removal insert 32 in the support 12', FIGS. 9 and 10. The shorter length of the lower leg of children presents a problem in getting the foot out the the X-ray beam. While it was indicated above that the foot could be turned to one side, the foot problem is also solved. In the case of an adult, by the fact that the heel extends beyond the end of the support 12, allowing the foot to readily drop to a lower angle where it does not interfere with the X-ray beam passing through the patella. By removing the insert 32, as illustrated in FIG. 8, a slot is created, into which the heel of a small child can drop to take his foot out of the beam field through the knee.

Another feature of the invention is illustrated in FIGS. 8–10, which enables further evaluation of the femoral-patella joint. In the previously described us of the present platform, the leg muscles have been relaxed. This relaxed condition is necessary for proper evaluation of the joint's condition and previously difficult to obtain. However, in many cases it is also desirable to evaluate the knee with the quadracepts muscles tensioned.

To this end, a pair of straps 34 are secured to the side members 16. The free ends of the straps are provided with Velcro fasteners. When a patient is positioned on the support 10', as described, The ends of the straps 34 are fastened together to restrain the lower leg from upward movement.

With the straps 34 in place, the patient can tension his quadracepts muscles. This tensioning action affects the relationship of the patella to femur joint, giving further information of importance in evaluating proper treatment. The ability to obtain repetitive X-rays of both the tensioned condition and relaxed condition of this joint in the same degree of flexion, is of great importance to the surgeon.

Figure 11:
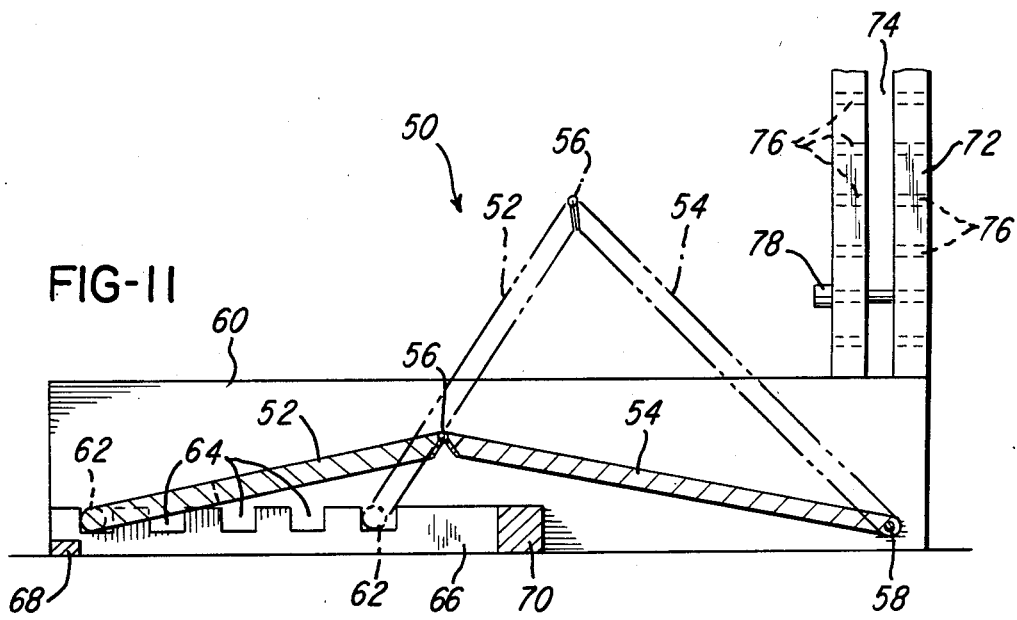
FIG. 11 is an elevation of a further positioning platform, with portions broken away and in section, embodying the present invention and providing means for varying the degree of flexion of a patients leg as it is X-rayed.
Figure 12:
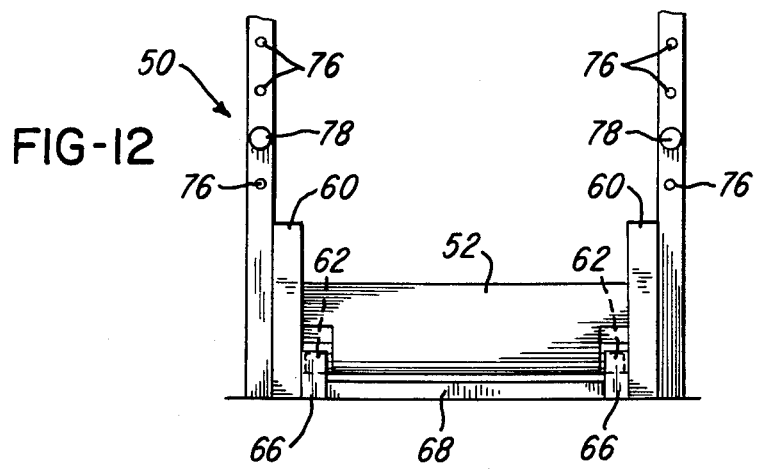
FIG. 12 is an end view of the positioning platform seen in FIG. 11.

While the fixed 40 deg. view is of great importance, other degrees of flexion are also employed in the evaluation of knee problems. FIGS. 11 and 12 illustrate a positioning platform 50 having such capability.

The platform 50 comprises a lower leg support 52 and a thigh support 54, angled relative to each other and connected at their apex by a hinge 56, which, preferably is formed of radiolucent material. The opposite end of the support 54 is pivotally mounted by pins 58 on side members 60. The opposite or lower end of the support 52 is provided with outwardly projecting lugs 62 whch may be selectively positioned in notches 64 formed in bars 66 secured to the inner surfaces, respectively, of the side members 60.

The side members 60 are connected by cross bars 68, 70, forming in combination therewith a base which positions the supports on the examination table.

Posts 72 are secured to the side members 60 and define a slot 74 for positioning an X-ray film cassette, as in the previous embodiments. In order to provide a greater range of vertical adjustment for the film cassette, a series of holes 76 is provided in each of the posts 72. Pins 78 are inserted in holes 74 of equal height to position a film cassette at a desired height within the slots 74. The lowest position of the cassette is defined by the side members 60, upon which the cassette will rest.

The platform 50 is particularly effective in the examination of a knee which has experienced trauma and is painful to flex. A patient may be placed on an examination table in a supine position with the supports 52, 54 in their positions of minimum flexion, as shown in full lines in FIG. 11. The supports may then be pivoted to a higher angle of flexion and set in that position by engagement of the lugs 62 with selected notches 64 in the bars 66.

The desired degree of flexion, up to as much as 110 deg. may be obtained progressively, so that undue discomfort for the patient is avoided. This end is also attained passively on the part of the patient. That is the patient is first placed in a supine position on the examination table. His leg can then be raised and the platform slid therebeneath. The leg may then be allowed to rest on the supports 12, 14 in their lower position of minimum flexion. The angle between the supports may then be increased to that desired for X-ray evaluation. All of this can be accomplished with the patient fully relaxed, thus minimizing, if not eliminating, the possibility of further trauma in obtaining an X-ray evaluation of the patient's problems.

As with the previous platforms, the platform 50 enables accurate, repetitive X-ray evaluation of the patella-femoral joint, which greatly enhances the value of such evaluation of the patient's problem and the progress made in its treatment.

Various modifications of the described embodiments will occur to those skilled in the art, within the spirit of the present inventio. For example the removable insert 32 and the restraining straps 34 shown in one embodiment could also be incorporated, with advantage, in the other embodiments. Other radiolucent materials could be employed, instead of the described use of wood. In fact, the portios of the positioning platform not within the field of view of the X-ray film need not necessarily be made of wood or other radioluscent material.

The scope of the invention is, therefore to be derived from the following claims.

Having thus described the invention, what is claimed as novel and desired to be secured by Letters Patent of the United States is:

1. A platform for positioning the leg of a patient in the taking of X-rays of the knee joint, said positioning platform comprising an upper leg support and a lower leg support joined at an apex, said supports being angled relative to each other from the apex to define the degree of flexion of the patient's knee when his leg is supported, and means for positioning an X-ray film cassette in a plane generally parallel to and spaced from a plane bisecting the angle between said supports.

2. A platform, for positioning the leg of a patient lying in a supine position on an examination table, as in claim 1 wherein said upper and lower leg supports are mounted on a base which positions their apex in spaced relation above the examination table and the cassette positioning means are disposed at one end of said base.

3. A positioning platform as in claim 2 wherein the cassette positioning means further comprise means for positioning the said cassette at selectable heights relative to the apex of the upper and lower leg supports.

4. A positioning platform as in claim 3 wherein the cassette positioning means comprise posts projecting upwardly from opposite sides of the base, said posts having vertically disposed slots for receiving the film cassette, and the means for positioning the cassette at selectable heights comprise a pair of blocks, respectively mounted on said posts, each block being rectangular with a length greater than its width, each block being pivotally mounted at one corner about an axis generally aligned with the slot of the post.

so that the blocks may be swung to positions wherein their widths are vertically disposed, and the cassette may rest thereon in a raised position, and the blocks may be swung to positions wherein their lengths are vertically disposed to support the cassette in a higher position.

5. A positioning platform as in claim 4 wherein the each of the positioning blocks have a notch in one edge providing a surface which may be brought into a horizontal position above the axis of the pivotal connection, so that the film cassette may be supported thereon in an intermediate elevated position.

6. A positioning platform as in claim 2 wherein said leg supports extend from said apex to a point spaced above the bottom of said base, and the angle of each support relative to the bottom of said base is approximately equal.

7. A positioning platform as in claim 6 wherein the angle between said supports, and the angle of flexion is approximately 40 degrees.

8. A positioning platform as in claim 6 wherein the film cassette positioning means is disposed at the upper leg support end of the base, and further comprising a removable insert at the outer end of the lower leg support, which, when removed, permits the heel of a patient of short stature to drop below the level of the support, thus facilitating the foot being disposed our of a position which would interfere with taking an X-ray of the knee joint.

9. A positioning platform as in claim 6 further comprising means for elevating the lower leg support end of the base, so as to tilt the platform relative to the examination table, to facilitate examination of the knee of a patient of short stature.

10. A positioning platform as in claim 8 further comprising means for elevating the lower leg support end of the base, so as to tilt the platform relative to the examination table, to facilitate examination of the knee of a patient of short stature.

11. A positioning platform as in claim 2 further comprising
means, disposed at the lower leg support, outwardly of said apex, for restraining upwardly movement of the patient's lower leg, so that the patient may tension his quadracepts for an X-ray evaluation of the knee joint in this condition, as well as in a relaxed condition of the muscles.

12. A positioning platform as in claim 2 further comprising
means for varying the angle between said upper and lower leg supports, to obtain a desired angle of flexion for X-ray evaluation.

13. A positioning platform as in claim 12 wherein
the upper and lower leg supports are joined by a hinge at their apex.

14. A positioning platform as in claim 13 wherein
the outer end relative to the apex of the upper leg support is pivotally mounted on the base and
means are provided for locking the outer end of the lower leg support at varying positions relative to said base as a function of the desired positions of said upper and lower leg supports.

15. A positioning platform as in claim 2 wherein
the leg supports are relatively narrow, of a width sufficient to support a single leg of the patient.

16. A positioning platform as in claim 15 wherein
the width of the platform is approximately 10 inches.

17. A positioning platform as in claim 6 wherein
the angle between the upper and lower leg supports is approximately 40 deg.
the lengths of said supports is between about 11½ inches and 13½ inches and the apex is approximately 8½ inches above the bottom of the base, and the outer ends of the supports are spaced approximately 4 inches above the bottom of the base.

18. A method of taking an X-ray of the patellar-femoral joint of a patient, in either the caudad or caphladad view, comprising the steps of
positioning the patient on an examination table in a supine position,
placing a positioning platform underneath the leg to be examined, said platform having an upper leg support on which the upper leg of the patient rests and a lower leg support on which the lower leg of the patient rests, said upper and lower leg supports being angled relative to each other from an apex aligned with the pivot axis of the patient's knee and defining the angle of flexion thereof,
said platform having means for positioning an X-ray film cassette in a plane generally parallel to and spaced from a plane bisecting the angle between said supports so that said cassette is in alignment with said leg and to one side of the knee, and
directing an X-ray beam in a generally horizontal direction through said knee to expose the film cassette disposed distally of the knee.

19. A method as in claim 18 wherein the platform further comprises means for restraining the patient's lower leg from upward movement and including the further steps of
restraining the patient's lower leg, so that the patient may flex his quadracepts muscles with the degree of flexion defined by said supports being maintained, and
exposing the X-ray film while the quadracepts are so tensioned.

20. A method as in claim 18 wherein the platform includes means for varying the angle between the upper and lower leg supports from a relatively low angle to a relatively high angle and including the further steps of
adjusting the upper and lower leg supports to a relatively low angle before positioning the patients leg thereon and then adjusting the angle therebetween to a higher, desired angle, so as to minimize the trauma discomfort experienced by the patient.

* * * * *